United States Patent [19]
Sonek

[11] Patent Number: 4,899,756
[45] Date of Patent: Feb. 13, 1990

[54] ARTICULATED NEEDLE GUIDE FOR ULTRASOUND IMAGING AND METHOD OF USING SAME

[76] Inventor: Jiri D. Sonek, 217 Ravine Ridge Dr. North, Powell, Ohio 43065

[21] Appl. No.: 221,029

[22] Filed: Jul. 18, 1988

[51] Int. Cl.⁴ .............................................. A61B 8/00
[52] U.S. Cl. ................................................ 128/662.05
[58] Field of Search .......... 128/660.05, 661.07–661.1, 128/662.05, 303 B, 329 R; 604/116, 117, 272

[56] References Cited

U.S. PATENT DOCUMENTS

| | | | |
|---|---|---|---|
| 4,029,084 | 6/1977 | Soldner | 128/662.05 |
| 4,058,114 | 11/1987 | Soldner | 128/662.05 |
| 4,318,413 | 3/1982 | Iimura et al. | 128/660.05 |
| 4,346,717 | 8/1982 | Haerten | 128/662.05 |
| 4,469,106 | 9/1984 | Harui | 128/562.05 |
| 4,576,175 | 3/1986 | Epstein | 128/662.05 |
| 4,582,061 | 4/1986 | Fry | 128/329 R |
| 4,722,336 | 2/1988 | Kim et al. | 128/303 B |
| 4,733,661 | 3/1988 | Palestrant | 128/303 B |
| 4,791,334 | 12/1988 | Brunnett | 128/303 B |

*Primary Examiner*—Francis Jaworski
*Attorney, Agent, or Firm*—Porter, Wright, Morris & Arthur

[57] ABSTRACT

A shoulder is connected to a transducer housing in substantial alignment with the plane of an ultrasound beam provided at one end of the housing. An ascending link is pivotally connected to the shoulder, a descending link is pivotally connected to the ascending link and a needle mount is pivotally connected to the descending link. The ascending link, descending link and needle mount are movable in substantial alignment with the plane of the ultrasound beam. The needle guide may be generally cylindrical and a disposable needle-receiving sleeve may be inserted into a guideway formed in the needle mount. Alternatively, the needle mount may be a disposable cube-like structure readily attachable to and detachable from the descending link. In the latter form, the needle mount is provided with a guideway slot defined by relatively spaced apart end walls of the mount which are generally equal in height to the width of the guideway defined by the space therebetween. In this manner, approximately a 45 degree angle may be obtained by a biopsy needle inserted into the guideway.

14 Claims, 2 Drawing Sheets

ARTICULATED NEEDLE GUIDE FOR ULTRASOUND IMAGING AND METHOD OF USING SAME

TECHNICAL FIELD

The present invention relates to apparatus for mounting and controlling the movement of a medical needle as it penetrates the body, and more particularly to such guide apparatus adapted for attachment to ultrasound imaging devices.

BACKGROUND ART

Ultrasonic imaging of maternal and fetal tissues has greatly facilitated prenatal diagnosis and treatment. Among other uses in this field, ultrasound devices provide images which assist the physician in properly positioning a biopsy needle to perform amniocentesis, cordocentesis and transabdominal chorionic villus sampling.

While relatively broad, the ultrasound beam is generally flat. As a result, it has been difficult to keep the biopsy needle within the plane of the ultrasound beam. Once it escapes this plane, the needle will not be seen on the screen.

Various attempts have been made in the past to assist the physician in keeping the biopsy needle in view so that it may be properly guided into an aminotic sack, umbilical cord or placenta. U.S. Pat. Nos. 4,058,114 issued Nov. 15, 1977 to Soldner, 4,469,106 issued Sept. 4, 1984 to Harui, 4,576,175 issued Mar. 18, 1986 to Epstein and 4,582,061 issued Apr. 15, 1986 to Fry disclose needle guiding apparatus adapted for attachment to the probe or transducer of an ultrasonic device. While all of these devices provided some movement of the needle guide and needle relative to the transducer, such movement was significantly limited to prevent the needle from escaping the plane of the ultrasound beam. As a result, the physician was significantly hampered in positioning the needle prior to and during insertion, as well as in positioning the transducer once the needle was inserted into the mother's abdomen. As to this latter limitation, it is desirable to change the position of the ultrasound transducer once the needle has been inserted so that the physician is able to get a different, and perhaps improved, image of the fetus and target area for further positioning of the needle, as well as for additional diagnostic work.

It has also been found that the preferred angle of penetration of the biopsy needle for reaching the selected maternal or fetal tissue is approximately 45 degrees from an imaginary perpendicular plane projecting upwardly from the point of entry on the maternal abdomen. This angle is also ideal for obtaining a clear image of the needle on the viewing device. While this "ideal" angle of penetration could be achieved with some of the prior art devices disclosed in the above-identified patents, it was rather difficult to establish. The contour of the maternal abdomen is obviously not planar, was difficult to guage the proper angle without distracting the physician's attention from other, more critical, matters. Further, the ultrasound transducer is frequently held in non-perpendicular positions relative to the patient's abdomen, so it was a poor reference for guaging the penetration angle. The prior art needle guides were so constructed that, in order to obtain a suitable entrant angle for the biopsy needle, the angle of the transducer relative to the maternal abdomen had to be severely restricted.

Accordingly, the present inventor was confronted with the problems of devising a needle guide which would assist in keeping the needle within the plane of the ultrasonic beam, which would permit greater movement — both of the biopsy needle prior to and during penetration and of the ultrasound transducer after penetration — and which would make it easier to establish an optimal entrant angle for the biopsy needle.

SUMMARY AND OBJECTS OF THE INVENTION

The present invention is an articulated needle guide for attachment to an ultrasound transducer which is capable of producing a generally planar ultrasound beam at one end of a transducer housing and a related method of using the subject needle guide. The articulated needle guide basically comprises a shoulder mountable on the transducer housing, an ascending link pivotally connected to the shoulder, a descending link pivotally connected to the ascending link and a needle mount pivotally connected to the descending link and provided with a needle-positioning channel extending therethrough. The shoulder is mountable on the transducer housing in substantial alignment with the ascending link, the descending link and the needle mount are movable in substantial alignment with the plane of the ultrasonic beam. Preferably, a coupling device is provided for readily attaching and detaching the needle mount from the second arm, and the needle mount is provided with relatively spaced apart side walls generally equal in height to the width of the needle-positioning channel defined by the space between the side walls.

The primary object of the present invention is to provide a device that keeps a biopsy needle within the plane of an ultrasonic beam as the needle penetrates a patient. Another important object of the present needle guide is to permit the ultrasonic transducer to be moved once the biopsy needle has penetrated the patient without losing an image of or disturbing the position of the needle. Yet another important object of the present invention is to permit substantial movement of the needle to accommodate various contours and characteristics of the patient while, at the same time, permitting the physician to position the needle for an optimal angle of penetration. Further objects and advantages of the present invention may become more readily apparent in light of the following drawings and description of the preferred embodiment.

BRIEF DESCRIPTION OF THE DRAWING

FIG. 1 also includes a fragmentary sectional view of a portion of a maternal abdomen and a diagrammatic view of a fetus and related maternal/fetal organs;

DETAILED DESCRIPTION OF THE PREFERRED EMBODIMENT

Figure 1:
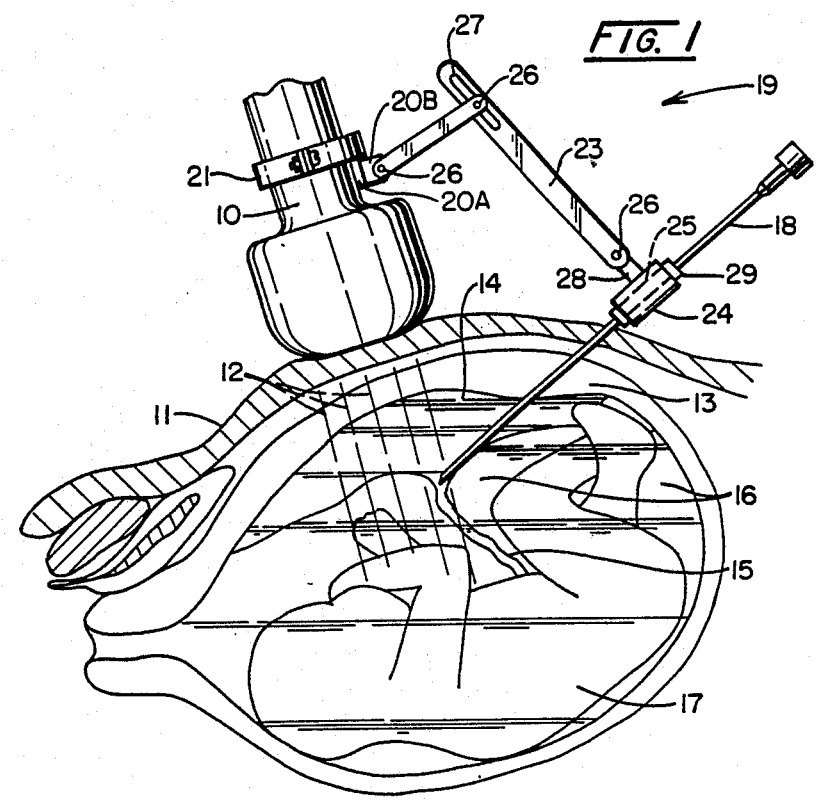
FIG. 1 is a side elevational view of an articulated needle guide according to the present invention, attached to an ultrasound transducer housing.

As indicated in the drawings, a housing 10 in which an ultrasonic transducer is disposed is typically brought into contact with a maternal abdomen 11 in order for an ultrasound beam 12 projecting from the transducer to scan maternal/fetal organs or tissues such as the uterine wall 13, the placenta 14, he umbilical cord 15, the amniotic sacks 16, and the fetus 17. In a manner of which those skilled in the art are aware, portions of the ultrasound beam 12 penetrate the various maternal and fetal organs, are reflected back to the transducer, and are converted into electronically generated, visual images of the tissues upon which the beam is focused. The beam 12 projecting from the transducer is generally planar. Thus, while a relatively wide and/or deep area of the patient and her baby may be visualized, the area is relatively flat due to the planar orientation of the beam 12. Accordingly, the image provided by the ultrasound equipment, while relatively deep in terms of the layers of tissue which are displayed, is also relatively flat, so the image is somewhat analagous to a sectional view of the tissue.

There are several prenatal diagnostic procedures which involve the penetration of a biopsy needle 18 through the maternal abdomen 11 and into various fetal/maternal organs from which cells and fluid are obtained. Amniocentesis requires amniotic fluid to be sampled from one or more of the amniotic sacks. Cordocentesis involves percutaneous umbilical cord blood sampling. Transabdominal chorionic villus sampling requires small amounts of tissue and fluid to be obtained from the placenta. As may be readily appreciated, the various organs illustrated in diagrammatic fashion in FIG. 1 are not to scale and may be much smaller and difficult to locate than represented in the drawing. Accordingly, ultrasound imaging technology has been of great assistance to physicians by making it possible to properly position the biopsy needle 18 for performing these diagnostic procedures. Basically, the ultrasonic equipment provides an image of the biopsy needle as it penetrates fetal/maternal tissue for so long as the needle remains in the relatively narrow plane of the ultrasound beam.

Figure 2:
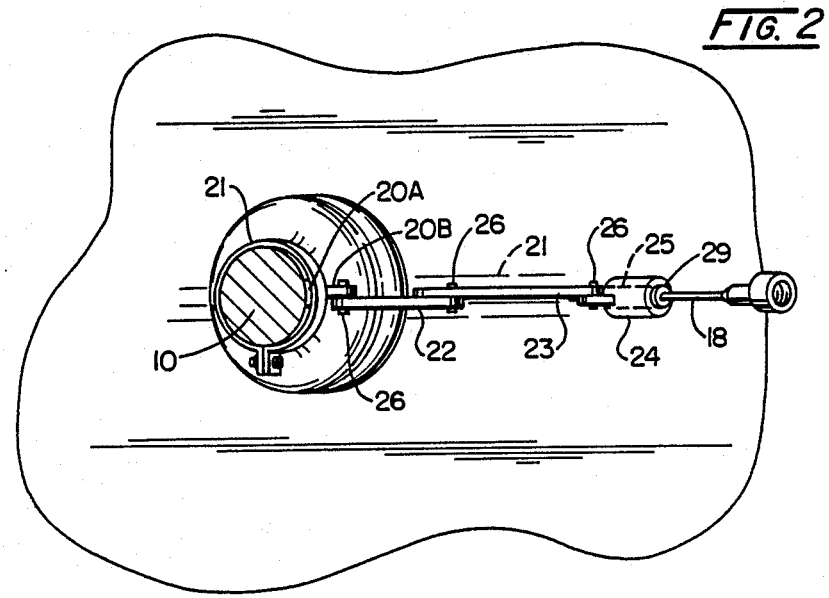
FIG. 2 is a top plan view of the present needle guide attached to a transducer housing, and particularly illustrates the alignment of the guide components with an ultrasonic beam generated by the transducer.

In order to maintain this alignment, the present articulated needle guide, generally designated 19, was invented. As indicated in FIGS. 1 and 2, the guide 19 basically comprises an anchor or shoulder 20A, 20B that may be removably secured to the transducer housing 10 by a connector 21 in substantial alignment with the plane of the ultrasound beam 12, an ascending link or arm 22 pivotally connected to the shoulder 20B, a descending link or arm 23 pivotally connected to the ascending link 22, and a needle mount or positioner 24 pivotally connected to the descending link 23 and provided with a channel or guideway 25. As best indicated in FIG. 2, the ascending link 22, the descending link 23 and the needle mount 24 are movable in substantial alignment with the plane of the transducer's ultrasonic beam 21.

Figure 3:
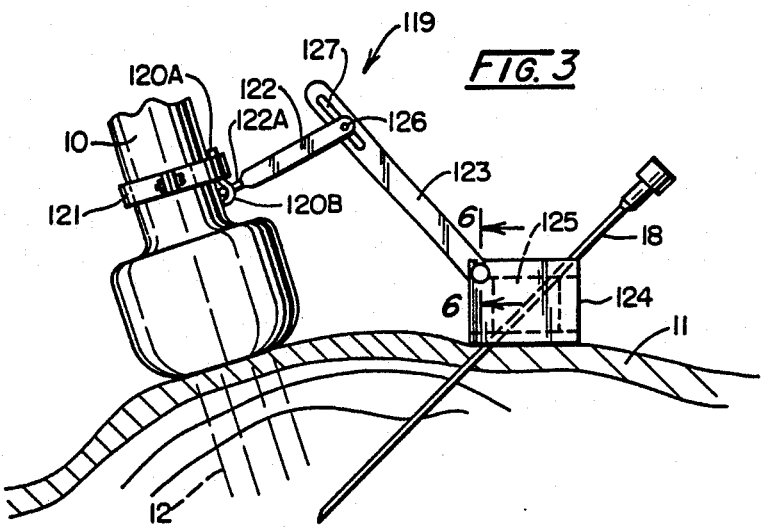
FIG. 3 is a reduced side elevational view similar to FIG. 1 and discloses a modified form of the present invention.

Typically, the connector 21 for securing the shoulder 20A, 20B to the transducer housing 10 is a stainless steel strap or band that may be tightened onto the neck of the transducer. An arcuate base portion 20A of the shoulder is sandwiched between the transducer neck and the strap 21. The shoulder is also provided with a flange portion 20B extending generally perpendicularly from the base 20A. Alternatively, as shown in FIG. 3, the shoulder may be formed with a link-receiving bend 120B.

The ascending arm 22, as indicated in FIGS. 1 and 2, is preferably a relatively short, and generally narrow and flat extension which may be formed from generally rigid synthetic resin or stainless steel material. The ascending link 22 is provided at each end thereof with a bore for receiving a pivot pin or rivet 26 by which the arm 22 is pivotally connected to the anchor 20B and to the descending arm 23. Alternatively, as indicated in FIG. 3, the first arm 122 may be formed with an L-shaped pin 122A at one end thereof, the right-angular portion of which is pivotally mounted in the space provided by the bend 120B in the anchor.

Figure 6:
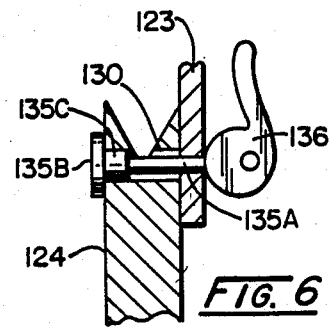
FIG. 6 is an enlarged vertical sectional view taken along line 6—6 of FIG. 3 and particularly illustrates components for readily attaching and detaching the modified needle mount to the rest of the present invention.
Figure 7:
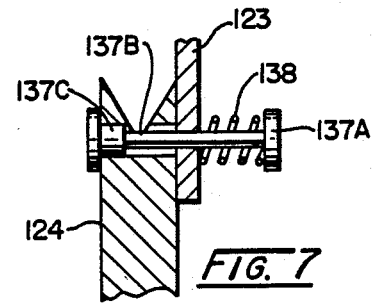
FIG. 7 is an enlarged vertical sectional view similar to FIG. 6 and illustrates alternative components for readily coupling the modified needle mount to the rest of the present invention.

As indicated in FIGS. 1 and 2, the descending arm 23 is preferably relatively elongated in comparison to the ascending arm 22, but is of approximately the same width and depth or flatness as the ascending link. A longitudinally extending, pin-receiving slot 27 may be advantageously provided in an end portion adjacent to the ascending link to increase the range of movement of the descending arm relative to the ascending arm, while maintaining the descending arm in substantial alignment with the plane of the transducer beam 12. In this manner, adjustment of the position of the needle mount 24 and biopsy needle 18 may be more easily accomplished on relatively obese patients. The end of the descending arm opposite to the slot 27 is provided with a bore and a pivot pin 26 by which the mount 24 is pivotally connected. Alternatively, as indicated in FIG. 3, the end of the descending arm 123 opposite the slot 127 may be provided with a quick coupling device such as illustrated in FIGS. 6 and 7 and described below.

As shown in FIGS. 1 and 2, the needle mount 24 is generally cylindrical and is provided with a radially extending flange 28 formed with a bore for pivotal attachment to the unslotted end of the descending arm 23. In this configuration, the guideway 25 takes the form of a longitudinally extending bore, and a sterile, disposable, synthetic resin sleeve 29 is preferably inserted into the bore 25 to maintain the sterility of the biopsy needle 18 as it is guided through the mount 24.

Figure 4:
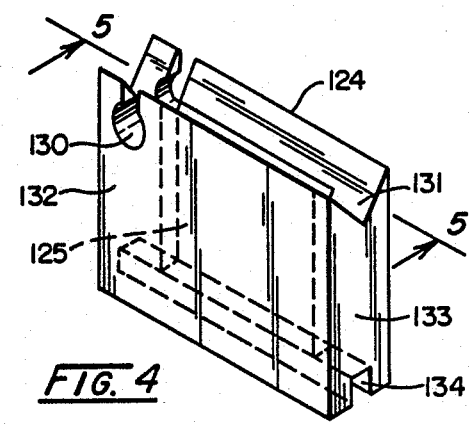
FIG. 4 is an enlarged perspective view of the needle mount on the modified guide shown in FIG. 3.
Figure 5:
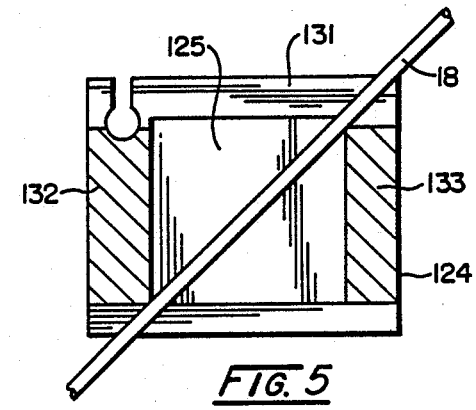
FIG. 5 is a vertical sectional view taken along line 5—5 of FIG. 4 and particularly illustrates the construction of the modified-needle mount shown in FIGS. 3 and 4.

Alternatively, and as indicated in FIGS. 3-7, the needle-receiving mount or housing 124 may be a relatively flat block formed with a relatively wide guideway 125. More particularly, as illustrated in FIGS. 4 and 5, the mounting block 124 is formed with a pin-receiving, keyhole-shaped slot 130 in one upper corner thereof, with a V-shaped groove 131 defining an upper, generally horizontal edge of the block, with a pair of relatively spaced apart, generally vertical end walls 132 and 133, and with a generally U-shaped channel 134 defining a lower, generally horizontal edge of the block. The end walls 132 and 133 are generally equal in length or height to the width of the guideway 125 defined by the space between the side walls 132, 133. In this manner, the physician can place the shaft or intermediate portion of the needle 18 in diagonal fashion through the guideway 125 and obtain approximately a 45 degree angle by engaging diagonally opposing corners or edges of the side walls with the needle shaft. The upper V-shaped channel 131 facilitates the entry of the needle tip 18A into the guideway or channel 125, and the lower U-shaped channel or furrow 134 permits the physician to insert the tip 18A completely through the guideway 125, thereby obtaining the desired 45 degree angle, while keeping the tip recessed from the lower surface of the block 124. In this manner, the maternal abdomen will not be scratched or cut by the needle tip 18A as the mounting block is moved into position over the patient.

Preferably, the needle mount 124 is readily detachable from the descending arm 123 and would be available as a sterile disposable item either in a package with or separately from the disposable, sterile biopsy needle 18. In order for the mount 124 to be readily attached and detached from the descending link 123, a pin 135 A, B, C, (FIG. 6) is mounted in the distal bore of the descending link 125. The pin is formed with a shaft 135A that is small enough in diameter to slip out of the upper opening in the keyhold slot 130. At one end of the pin, however, is an enlarged head 135B and a collar 135C. The collar 135C is sufficiently large to be trapped in the slot 130. A levered cam 136 is rotatably mounted at the opposite end of the pin shaft 135A and may, in the usual manner, be shifted in position to force the collar 135C into the slot 130. Thus, the adjacent end of the descending arm 123 is removably and pivotally connected to the needle mount 124. Alternatively, as indicated in FIG. 7, a pin 137A, B, C may be provided on the descending arm 123. An enlarged head 137A and a spring 138 may be provided to bias the shaft 137B in a direction which forces the enlarged shank or collar 137C into the keyhole slot 130 in the mounting block 124. Thus positioned, the collar 137C prevents the block 124 and link 123 from separating.

The present articulated needle guide is operated and used in the following manner. The band 21, 121 is loosely fastened onto the transducer housing 10 and the base 19A, 119A of the shoulder is positioned between the band and the housing so that the flange 19B or bend 119B is aligned with the plane of the ultrasonic beam 12. The band 21, 121 is then tightened to secure the anchor 20, 120 in the desired position. The ascending and descending arms 22, 122 and 23, 123, respectively, are pivotally connected together by a rivet or pin 26, 126, either prior to packaging or upon attachment to the transducer housing. Likewise, the rivet or pin 26 connecting the flange 19B to the ascending arm 22 may already be provided or may be added upon installation. However, in the case of the alternative form of the ascending arm 122 illustrated in FIG. 3, the right angular portion 122A is inserted into the bend 129B in the anchor prior to tightening the band 121. In any event, care must be taken by the assembler to align the ascending and descending links with the plane of the transducer beam 12. The needle mount 24 illustrated in FIGS. 1 and 2 is pivotally attached to the descending arm 23 by a pin or rivet 26 either prior to packaging or during installation, and the sterile sleeve 29 is simply inserted into the needle-receiving bore 25. In the case of the mounting block 124 illustrated in FIGS. 3-7, however, attachment occurs after the upstream arms and other components are installed. Attachment of the block 124 to the descending arm 123 is accomplished in the manner described above in connection with the coupling devices illustrated in FIGS. 6 and 7.

Once the present articulated needle guide, in either of its alternative forms is assembled, the physician or staff member conducts the usual antiseptic procedures and activates the ultrasonic device and positions the transducer 10 so that an image of the target area is provided. The biopsy needle 18 is then inserted into the guideway 25, 125 of the mount 24, 124 without exposing the tip 18A, and the positions of the mount and ascending and descending arms are pivotally and/or slidably shifted. When the physician is satisfied that the needle is disposed over the correct portion of the maternal abdomen and that the correct angle of penetration is established for the desired fetal/maternal organ to be reached, the needle is inserted while being viewed on the visual display unit of the ultrasound equipment until a desired position is reached. The physician or an assistant may then hold the needle 18 and mount 24, 124 stationary while the position of the transducer on the maternal abdomen is shifted to provide a different image of the target area or of other maternal/fetal organs of concern. Once the physician is satisfied that the biopsy needle is properly located, the desired tissue sample is obtained and the needle is withdrawn.

Thus it may be seen that the present articulated needle guide provides a substantial range of movement for properly locating the biopsy needle and for shifting the position of the transducer after penetration of the needle without losing the image of the needle on the display apparatus. In addition, the present invention may be constructed so as to assist the physician in establishing an optimal angle of penetration for the biopsy needle and in maintaining the sterility of the procedure.

While alternative embodiments of the present invention have been illustrated and described in some detail, the foregoing disclosure is not intended to unduly limit the spirit of the invention or the scope of the following claims.

I claim:

1. An articulated needle guide for use with an ultrasound imaging device that generates a generally planar ultrasound beam at one end of a transducer housing, said articulated needle guide comprising: a shoulder mountable upon the transducer housing in substantial alignment with the plane of the ultrasound beam, a first link pivotally connected to the shoulder, a second link pivotally connected to the first link, and a needle mount pivotally connected to the second link and formed with a needle-receiving guideway through which a needle may be inserted into a subject; said needle mount and said transducer housing being wholly movable in substantial alignment with the plane of the ultrasound beam, respectively, prior to and after inserting the needle into the subject.

2. An articulated needle guide according to claim 1, wherein the first link is readily attachable to and detachable from the shoulder.

3. An articulated needle guide according to claim 1, wherein the needle mount is readily attachable to and detachable from the second link.

4. An articulated needle guide according to claim 3, wherein the needle mount is generally cube-shaped and provided with relatively spaced apart end walls approximately equal in height to the width of the guideway defined by the space between said end walls.

5. An articulated needle guide according to claim 4, wherein the needle mount is formed along an upper edge thereof with a generally V-shaped groove and along a lower edge thereof with a channel, and wherein the guideway opens onto said V-shaped groove and said channel.

6. An articulated needle guide according to claim 3, wherein coupling means are provided on the second link for readily attaching and detaching the needle mount.

7. An articulated needle guide according to claim 1, wherein the needle mount is generally cylindrical, and a disposable sleeve is provided for the guideway formed therein.

8. An articulated needle guide according to claim 1, wherein a longitudinally extending slot is provided at one end of the second link and wherein a pin extends through said slot and into a bore formed in the first link to connect said second link and said first link together.

9. A method of positioning a needle for visualization with an ultrasound imaging device which generates a generally planar ultrasound beam at one end of a transducer housing, said method comprising the steps of:
(a) attaching to the transducer housing a shoulder portion of an articulated needle guide, said articulated needle guide comprising the shoulder portion, a first link pivotally connected to said shoulder portion, a second link pivotally connected to the first link, and a needle mount pivotally connected to the second link, said transducer housing and needle mount being wholly movable substantially within the plane of the ultrasound beam;
(b) inserting a tip portion of the needle into a guideway extending through the needle mount;
(c) positioning the transducer housing so that a first image of a desired target area is provided;
(d) positioning the needle mount so that a desired location and a desired angle of entry of the needle are obtained;
(e) inserting the needle through the needle mount and into the desired target area; and
(f) repositioning the transducer housing to obtain a second image of the desired target area.

10. The method according to claim 9, which includes inserting a sterile, needle-receiving sleeve into the guideway of the needle mount.

11. The method according to claim 9, which includes attaching a readily removable and disposable needle mount to the second link.

12. The method according to claim 11, which includes providing the needle mount with a needle-receiving guideway defined by a pair of relatively spaced apart end walls generally equal in height to the space therebetween.

13. The method according to claim 12, which includes positioning a tip portion of the needle in a lower corner of the guideway, said lower corner being defined by one of the end walls and by a channel extending along a lower edge portion of the needle mount.

14. The method according to claim 13, which includes resting an intermediate portion of the needle on a diagonally opposing corner of the guideway, said opposing corner being defined by the opposing end wall and by a V-shaped groove extending along an upper edge of the needle mount.

* * * * *